United States Patent
Clemenz et al.

(10) Patent No.: US 10,398,856 B2
(45) Date of Patent: Sep. 3, 2019

(54) ACCESS DEVICE

(71) Applicant: Hahn-Schickard-Gesellschaft Fuer Angewandte Forschung E.V., Villingen-Schwenningen (DE)

(72) Inventors: Markus Clemenz, Villingen-Schwenningen (DE); Thomas Lorenz, Hornburg (DE); Michael Kegel, Tennenbronn (DE)

(73) Assignee: Hahn-Schickard-Gesellschaft Fuer Angewandte Forschung E.V., Villingen-Schwenningen (DE)

( * ) Notice: Subject to any disclaimer, the term of this patent is extended or adjusted under 35 U.S.C. 154(b) by 174 days.

(21) Appl. No.: 15/036,296

(22) PCT Filed: Nov. 14, 2013

(86) PCT No.: PCT/EP2013/073883
§ 371 (c)(1),
(2) Date: May 12, 2016

(87) PCT Pub. No.: WO2015/070914
PCT Pub. Date: May 21, 2015

(65) Prior Publication Data
US 2016/0296715 A1    Oct. 13, 2016

(51) Int. Cl.
*A61M 5/46*    (2006.01)
*A61M 5/32*    (2006.01)
(Continued)

(52) U.S. Cl.
CPC .............. *A61M 5/46* (2013.01); *A61M 5/168* (2013.01); *A61M 5/3232* (2013.01);
(Continued)

(58) Field of Classification Search
CPC .... A61M 5/46; A61M 5/3293; A61M 5/3287; A61M 5/3232; A61M 2005/1585; A61M 2005/14252
See application file for complete search history.

(56) References Cited

U.S. PATENT DOCUMENTS

| 5,437,640 A | 8/1995 | Schwab |
| 5,591,138 A | 1/1997 | Vaillancourt |

(Continued)

FOREIGN PATENT DOCUMENTS

| AU | 8704582 A | 9/1983 |
| GB | 2436526 B | 1/2010 |

(Continued)

OTHER PUBLICATIONS

European Patent Office International Search Report and Written Opinion of the International Searching Authority for PCT/EP2013/037883 dated Apr. 3, 2014 (11 pages).

*Primary Examiner* — Nathan R Price
*Assistant Examiner* — Anh Bui
(74) *Attorney, Agent, or Firm* — Harris Beach PLLC; Laure W. Smalley

(57) ABSTRACT

The invention relates to an access device comprising: a base (1) for aligning the access device with the skin of a patient; a needle for puncturing the skin, the needle comprising a hub (2) and a cannula (10), and the needle being movably mounted in the base (1) such that it can move between a first, fully retracted, and a second, maximally extended, position; and a locking mechanism which engages when the needle retracts from the second position and reaches a discrete third position, inhibiting the needle from further retracting to the first position. According to the invention, the access device is actuatable to disengage the locking mechanism.

12 Claims, 8 Drawing Sheets

(51) Int. Cl.
*A61M 39/02* (2006.01)
*A61M 5/168* (2006.01)
A61M 5/142 (2006.01)
A61M 5/158 (2006.01)

(52) U.S. Cl.
CPC ........ *A61M 5/3287* (2013.01); *A61M 5/3293* (2013.01); *A61M 39/02* (2013.01); *A61M 2005/14252* (2013.01); *A61M 2005/1581* (2013.01); *A61M 2005/1585* (2013.01); *A61M 2005/1586* (2013.01); *A61M 2005/1587* (2013.01)

(56) References Cited

U.S. PATENT DOCUMENTS

| | | |
|---|---|---|
| 7,556,615 B2 | 7/2009 | Pettis et al. |
| 2002/0077599 A1 | 6/2002 | Wojcik |
| 2003/0171716 A1* | 9/2003 | Ejlersen ............... A61M 5/427 604/117 |
| 2004/0147901 A1* | 7/2004 | Py ....................... A61M 5/2033 604/506 |
| 2007/0191780 A1 | 8/2007 | Modi |
| 2008/0269687 A1 | 10/2008 | Chong et al. |
| 2013/0041318 A1* | 2/2013 | Vosseler ............. A61M 5/3287 604/117 |

FOREIGN PATENT DOCUMENTS

| | | |
|---|---|---|
| WO | WO-02/100457 A2 | 12/2002 |
| WO | WO-03072172 A2 | 9/2003 |
| WO | WO-2004004803 A2 | 1/2004 |
| WO | WO-2007/061972 A2 | 5/2007 |
| WO | WO-2009/086463 A1 | 7/2009 |

\* cited by examiner

ACCESS DEVICE

CROSS-REFERENCE TO RELATED APPLICATIONS

This application is a national stage application under 35 U.S.C. § 371 of PCT Application No. PCT/EP2013/073883, entitled "Access Device", filed Nov. 14, 2013.

FIELD OF THE INVENTION

The invention relates to an access device comprising a base for aligning the access device with the skin of a patient; a needle for puncturing the skin, the needle comprising a hub and a cannula, and the needle being moveably mounted in the base such that it can move between a first, fully retracted, and a second, maximally extended position.

BACKGROUND OF THE INVENTION

The US-document US 2013/0041318 A1 discloses a dermal access device for fluid injection. A hollow needle is arranged at a slider which is movably connected to a bearing block which can be fixated on the skin of a patient. The device allows puncturing the skin with the needle at an angle and applying an intradermal injection.

From the US-document U.S. Pat. No. 7,556,615 B2, for example, a microneedle access device is known which is provided with a protruding ring-shaped skin pre-stressing device. This skin pre-stressing device encloses the microneedle, and it touches the skin surface of the patient before puncturing the skin, shortly after the microneedle deformed the skin through contact. With the ring-shaped skin pre-stressing device, the deformation of the skin surface is minimized, which allows for a more precise penetration of the microneedle.

Further, from the international patent application publication WO 2007/061972 A2 an access device for injectable substances is known, that is provided with a hollow needle of sufficient length in order to penetrate into the skin of a patient. The access device is provided with a delimiter for controlling the penetration depth of the hollow needle as well as a stabilizer that is positioned at a distance to the delimiter. Deformation of the tissue close to the puncture position is avoided with the stabilizer, so that the depth where the substance is introduced is essentially determined through the length of the hollow needle.

The US-document US 2004/0147901 A1 discloses an intradermal application device, provided with a vacuum chamber in order to achieve an essentially flat puncture area for the hollow needle on the skin. The angle between the axis of the device and the skin is 45° in one embodiment, but can be every angle between 30° and 60° in other embodiments.

From an international patent application publication WO 2009/086463 A1 a device for applying a substance is known, which is provided with a sealed package with a squeezable reservoir, containing the substance. Further, a hollow needle is envisioned for the application of the substance, which is a therapeutic liquid.

The international patent application WO 02/100457 A2 discloses an insertion device and insertion set. The insertion device for inserting at least a portion of at least one piercing member of an insertion set through the skin of a patient includes a device housing, a carrier body and a driver. The carrier body is slidably received within the device housing for movement between an advanced position and a retracted position. The carrier body also includes a receiving structure to support the insertion set in a position with the at least one piercing member oriented for insertion through the skin of the patient at a predetermined or variable angle relative to the skin of the patient upon movement of the carrier body from the retracted position to the advanced position.

The patent application US 2008/0269687 A1 describes various patches for medical devices. An adhesive patch of a medical device may have selective areas with adhesive material of varying adhesion strengths. A medical device may include a pierceable membrane containing an agent, the pierceable membrane position to be pierced by a needle and to cause some of the agent to be carried to the user-patient.

In the UK patent application GB 2436526 A, a device for at least partially inserting a needle into the body of a patient is disclosed. The device comprises a connector adapted for attachment to a needle and a guard member having a guide surface adapted to rest against a surface of the skin. The connector is adapted to set an attached needle with a fixed position relative to the guard member, such that movement of the guide surface along the surface of the skin at least partially inserts the needle into the body.

The United States patent U.S. Pat. No. 5,437,640 describes a device for guiding the insertion of a hypodermic, tuberculin or other needle and, more particularly for administering a Mantoux tuberculin test. The device comprises a platform having a channel extending there through sized to receive a flexible needle for guiding the insertion of the needle at a prescribed angle, direction and depth for the introduction or removal of fluids from the body.

The US patent application US 2002/0077599 A1 discloses a low-profile inserter for an angled infusion set comprising an inserter housing having a bottom wall, a retainer slidably connected to the inserter housing for movement between retracted and extended position in a direction substantially parallel with the bottom wall and a base member connected to the inserter housing. The retainer is adapted to releasably receive a cannula assembly, including a cannula connected to a cannula housing. The base member has a lower surface that is adapted to contact a skin outer surface.

A novel device and method for intradermal delivery of an active agent is provided in the patent application US 2007/0191780 A1. The device comprises a housing, which contains a reservoir chamber. A flexible reservoir containing the active agent is placed in the chamber. Upon pressure on an actuator the active agents are delivered via a hollow needle to the skin.

The Australian patent AU 8704582 A discloses a wedge shaped structure, on which a syringe is placed. The syringe is drawn back against a spring means to cock the syringe in an activated position. The spring means is released and the syringe accelerates. The force injects the needle into the body. The fluid in the syringe is then dispensed.

Problem To Be Solved By The Invention

It is an object of the present invention to provide an improved access device. Particularly an access device which facilitates the application of injections and/or infusions with accurate and repeatable depth of penetration, allowing also untrained persons to administer such injections and/or infusions with a reduced or no risk of injury of the patient or user.

Solution According To The Invention

The reference numbers in all claims have no limiting effect but only serve the purpose of improving readability.

For solving the problem the invention teaches an access device according to the preamble of claim 1, wherein the access device is actuatable to disengage the locking mechanism. An achievable advantage of making the access device actuatable to disengage the locking mechanism is that the cannula can be fully or partially retracted before the access device is removed from the skin of a patient.

An access device according to the invention is an apparatus for injecting a fluid into the body or a body part of a patient for medical or non-medical (for example aesthetic) purposes. The targeted part of the body into which the injection is applied can for example be the cutis (dermis and epidermis) and/or subcutis and/or muscle tissue and/or a vein and/or an organ and/or any other body part accessible with a cannula. The term injection in the context of the invention also comprises infusions as well as the extraction of a body fluid or material (for example a biopsy). A patient in the context of the present invention is an entity that receives an injection and can be for example a human, an animal or a plant. The application of the injection is carried out by a user, for example a physician, a nurse, a paramedic, a non-medical practitioner, an untrained person or the patient himself or herself for example which is often the case for insulin injections. The access device advantageously allows safely performing injections with high precision and repeatability, meaning that the puncture angle and depth of the injection can be controlled accurately. In the context of the present invention, the term skin refers to a surface of the body or a body part of a patient to which the access device is applied and includes but is not limited to the dermis, mucosa, fascia, the fur of an animal, the exoskeleton of an insect or spider, scales of a fish, the bark of a tree and/or the surface of a leaf.

The access device comprises a base and a needle. The base may serve as a mechanical frame for alignment, guiding and protection of the needle and/or protection of the user and patient. The needle is to be understood as a needle commonly used with a syringe or an infusion line for carrying out an injection. The needle is movably mounted in the base such that it can move back and forth, mechanically guided by the base. The length of the stroke of the needle is defined by a first and a second position, limited by the base. The needle comprises a cannula and a hub, the cannula being a thin hollow tube. The hub is usually located at an end opposite a tip of the cannula and may provide a connection fitting for connection of for example a syringe or an infusion line. The hub can also be located anywhere in between the two ends of the cannula.

The needle is in the first position if no external force is applied to the needle. Then the needle is in its fully retracted state. Advantageously, in this position at least the tip of the cannula is shielded by the base. This has the achievable advantage that the user and the patient are protected from unwanted exposure to the cannula and the cannula is kept clean. By applying a manual force the needle can be moved towards the second position. In the second, maximally extended, position the cannula protrudes maximally from the bottom surface of the base. Here, maximally is to be understood as within the limitations of the motion mechanically limited by the base. From the second position, the needle can be retracted back towards the first position. While retracting, the needle reaches a third position, which is located between the first and the second position. In the third position the cannula is slightly retracted compared to the second position. Within the context of the invention, the needle in the access device does not need to be limited to only three discrete positions.

The access device further comprises a locking mechanism which is adapted to engage when the needle is retracted from the second position back towards the first position and reaches the third position. The locking mechanism prevents the needle from retracting further, keeping the needle in the third position. According to the invention, the access device is actuatable to disengage the locking mechanism. The access device may be actuated directly, for example by providing the access device with a separate switch or actuator or by making a part of the device actuatable, for example the hub of the needle, a part of the base or a movable part of a housing that covers the access device. Alternatively, the access device may be actuatable indirectly, for example via a fluid reservoir connected to the access device. In particular the access device may be actuatable manually by the user, for example by pressing, moving or turning a part of the access device. Disengaging the locking mechanism advantageously allows the needle to continue being retracted towards the first position.

After puncturing and penetrating the skin by moving the needle all the way from the first to the second position and then partially retracting the needle to the third position, the excess puncturing channel advantageously helps absorbing the injected fluid. The third position advantageously maintains a puncturing channel long enough so that the skin sufficiently seals the cannula in order to prevent leakage of the fluid. Wrinkles in the skin that may be created during the initial puncturing due to the resistance of the skin to the cannula can advantageously be reduced when partially retracting the needle to the third position. This can also make the injection less painful to the patient.

The invention is further solved by an access device according to the preamble of claim 3, wherein the locking mechanism comprises a cam and a cam follower that are adapted to convert the motion of the needle with respect to the base into an auxiliary action. An achievable advantage of causing an auxiliary action induced by the relative motion of the needle with respect to the base is that this action can be implemented without requiring an interaction by the user.

According to the invention, a cam is a feature such as a plate or a block with a designed contour which converts the relative motion of the needle with respect to the base into a motion of a cam follower in a transversal direction. Within the context of the invention, the motion of the cam follower does not need to be limited to only transversal directions, and comprises for example also rotational movements, for example leading to rotational movements of the hub or the needle, for example about the main symmetry axis of the hub or the needle. The cam follower is designed to follow the contour of the cam and its motion causes the auxiliary action. The auxiliary action is an effect that occurs as a result of the motion of the cam follower.

The problem is further solved by an access device according to the preamble of claim 8, wherein the hub of the needle has a connection fitting. A connection fitting can be of the Luer type, for example Luer-lock or it can be a connection fitting for connecting an injection pen or a cartridge holding injection system. Connection fittings may comprise a cannula for piercing a container or a membrane, thereby releasing or gaining access to a medical or non-medical substance. Providing a connection fitting can have the achievable advantage, that the access device can be used with a wide range of standardized syringes and tubes used for medical or non-medical treatments. General descriptions relating to the method of intradermal injections disclosed in US-document US 2013/0041318 A1 hereby incorporated herein by reference.

PREFERRED EMBODIMENTS OF THE INVENTION

In a preferred embodiment of the invention, the locking mechanism of the access device is adapted to inhibit the needle also from moving towards the second position. Therefore, the locking mechanism—when engaged—inhibits motion of the needle in both moving directions and locks the needle in the third position. Thus, it can be advantageously achieved that when a syringe is connected to the needle and an injection is made, the pressure from pushing the plunger of the syringe does not force the needle again towards the second position. This way, the injection can be administered at the desired penetration depth of the third position and unnecessary pain and discomfort for the patient can be avoided.

In a preferred embodiment of the invention, the cam is arranged on the hub and the cam follower is arranged on the base. A preferred cam is crafted in a single piece with the hub, for example by injection molding, rapid prototyping, 3D printing or scan LED technology. Preferably, the cam also assures a preferred orientation of the needle. In a preferred orientation of the needle, the sharp tip of the needle bevel is facing towards the skin and the bevel opening faces away from the skin. This way, an injection, in particular the puncturing of the skin can advantageously be less painful for the patient. In another preferred orientation of the needle, the bevel opening faces towards the skin. In a further embodiment of the invention, the position of the bevel opening is not defined. In an alternative embodiment, the cam is arranged on the base and the cam follower is arranged on the hub. In an alternative embodiment, the cam follower leads to a rotational movement of the hub or the needle. It is preferred that the hub further comprises a lock notch as part of the locking mechanism. It is preferred that a lock pin is arranged at the base as a counterpart for the lock notch. Alternatively the lock notch is arranged in the base and the lock pin is arranged in the hub.

It is preferred that the auxiliary action can only occur for one direction of motion of the needle with respect to the base. A preferred motion of the needle is a linear motion. Further it is preferred that the linear motion is along a main symmetry axis of the needle, where a preferred needle is essentially oriented along a straight symmetry axis. Preferably, the cam has two sides with different contours. It is preferred that the cam follower is in contact with the first contour for the first direction of motion from the first towards the second position. More preferably, the cam follower is in contact with the second contour for the second direction of motion from the second position back towards the first position. Preferably, the cam follower is adapted to automatically, i.e. without interaction by the user, switch from the first to the second contour when the needle is in the proximity of the second position. More preferably, two different auxiliary actions can occur for the two different directions of motion of the needle with respect to the base. The first auxiliary action occurs during the first direction of motion from the first towards second position and the second auxiliary action occurs during the second direction of motion from the second towards the first position. Even more preferably more than two different auxiliary actions can occur. Alternatively, the motion of the needle has a rotational component. Preferably the motion of the needle has a translatory and a rotational component. In such an embodiment, a preferred needle is at least in some states of motion at least partly curved. Preferably, a partly rotational, partly translatory motion of the needle is implemented by sliding the needle along a curved path, for example provided by a curved surface of the base. Injecting the needle into the body of the patient with a motion that is partly rotational may advantageously allow reaching a target tissue in the patient's body with a puncture angle that is different to the angle of a connection fitting as described further below. Another achievable advantage may be that such an injection can be carried out while avoiding particularly sensitive parts of the body, thus minimizing discomfort and/or pain for the patient. In an alternative embodiment, the rotational component of the needle movement happens around the main symmetry axis of the needle.

In a preferred embodiment of the invention, the auxiliary action is to prevent the engagement of the lock mechanism when the needle is moving from the first to the second position. Preferably the lock mechanism comprises a lock pin and a lock notch. In a preferred embodiment, the auxiliary action is that the lock pin is prevented from engaging with the lock notch. Advantageously an auxiliary action that prevents the locking mechanism from engaging when the needle moves from the first to second position allows puncturing the skin with the cannula of the needle without disruption but engages when the needle retracts to the third position.

In a preferred embodiment of the invention, the hub of the needle has a connection fitting. A preferred connection fitting is a Luer type connection fitting. Preferably, the Luer type connection fitting is a Luer-lock connection fitting. Preferred Luer-lock fittings are manufactured according to the industry standard ISO 594. Another preferred connection fitting is adapted for connection of an injection pen or a cartridge-holding injection system. A preferred injection pen is an insulin injection pen. Preferred injection pens include for example injection pens manufactured by B. Braun (for example Omnican Pen or Omnif ill Pen) or Becton Dickinson (for example BD Pen Classic, BD Pen Colour, BD Pen Ultra) or Berlin Chemie (for example BerlinPen or BerliPen) or Eli Lilly (for example Huma Pen Ergo or Huma Pen Sawio or HumaPen Luxura or HumaPen Memoir or Humalog KwikPen) or Haselmeier (for example DIAPEN) or Novo Nordisk (for example Novo Pen or NovoPen or FlexPen or FlexTouch or PenMate or InnoLet) or Owen Mumford (for example Autopen) or Sanofi-Aventis (for example OptiPen or ClickStar or Opticlik or TactiPen) or Ypsomed (for example D-Pen or ypsopen) or Pendiq. Preferred connection fitting for connecting a pen are manufactured according to the industry norm DIN EN ISO 11608-2:2012-12. Preferably a connection fitting for connecting a pen is a threaded fitting. An alternative connection fitting provides a bayonet fitting. Preferably a connection fitting also provides a cannula for piercing a container or a membrane to be connected via the connection fitting to the access device, thereby gaining access to a or releasing a medical substance. Providing a connection fitting can have the achievable advantage, that the access device can be used with a wide range of standardized syringes, infusion lines, injection pens and/or tubes used for medical or non-medical treatments.

A preferred needle comprises a cannula made of steel, preferably surgical stainless steel. Alternatively, the cannula is made of plastic or titanium or another material. . A preferred needle comprises one or more bevels at the tip to further facilitate puncturing of the skin. The tip of the cannula is the end used to puncture the skin of the patient. In an alternative embodiment the hub is located in between the two ends of the cannula. In another preferred embodiment of the invention, the cannula is beveled at the end opposite the tip, even more preferably both ends of the cannula are beveled. Preferably, the end of the cannula opposite the tip is adapted to pierce a sealing element of a cartridge containing a medicament, a medical or a non-medical substance. Preferred inner diameters of the cannula range from 0.08 mm to 3.8 mm.

According to a preferred embodiment of the invention, the needle is arranged at an angle with respect to a preferably essentially flat bottom surface of the base. This angle defines a puncturing angle with which the needle punctures the skin of a patient. Preferably, the puncturing angle is smaller than a right angle with respect to the surface of the skin in order to reproduce the way a physician would pierce the skin for an intradermal injection. Advantageously, the essentially flat bottom surface of the base facilitates alignment of the access device with the skin of a patient. In the simplest case this is achieved by manually applying the access device onto the skin of the patient. In a preferred embodiment of the invention, the needle creates a puncture angle with respect to the skin surface when puncturing the skin, the puncture angle not exceeding 60°. More preferably the puncture angle does not exceed 50°, even more preferably 30°. In one embodiment the puncture angle is between 30° and 60°, even more preferably between 40° and 50°. Even more preferably the puncture angle is approximately 45°. In an alternative embodiment, the puncture angle is between 5° and 25°, more preferably between 10° and 15°. Even more preferably the puncture angle is approximately 10°. In yet another embodiment, the puncture angle is between 70° and 110°, preferably between 80° and 100°, for example approximately 90°. Advantageously, the access device guides the needle to puncture the skin with a puncture angle that a physician would use for application of a dermal injection. In the context of the invention, degrees are to be understood with respect to a full circle of 360°. It is preferred that in the first position the cannula does not protrude from the base. This way, a risk of a user or patient coming in unwanted contact with the needle can be reduced.

In one embodiment of the invention, the base of the access device comprises adhesive means for fixating the base on the skin of the patient. Preferably, the adhesive is arranged at the bottom surface of the base which comes into contact with the skin of the patient. A preferred adhesive is a pressure sensitive adhesive. Alternatively, a moisture sensitive adhesive is used. A preferred adhesive means is covered by a removable film that protects the adhesive before use. An adhesive means advantageously allows fixating and securing the access device on the skin of the patient prior to puncturing the skin with the needle. A preferred adhesive allows removing the access device from the skin of the patient with very little discomfort after use. Alternatively, the bottom surface of the base has a structure that prevents slipping of the access device simply by pressing it onto the skin of the patient for example with a finger or the thumb. An alternative adhesive means is an adhesive bandage attached to the sides of the base. In another preferred embodiment, the access device is provided with an adhesive surrounding the dermal access device. In another preferred embodiment, no adhesive means are provided with the base. In this embodiment, the access device can be manually applied and aligned with the skin of the patient. Advantageously, the user applies the access device with one hand to the skin of a patient and with the other hand engages the injection, for example by pushing a plunger of a syringe.

It is preferred that the cannula of the needle of the access device is adapted to protrude no more than 100 mm in axial direction from the bottom surface of the access device. More preferably, the cannula is adapted to protrude no more than 50 mm, even more preferably no more than 10 mm. Advantageously the cannula protrudes thus far from the bottom surface of the access device, so that in the intended use, the tip of the cannula penetrates the skin less than 1.5 mm under the surface of the skin, more preferably less than 1 mm, measured perpendicularly to the surface of the skin. In an alternative embodiment of the invention, the cannula penetrates the body of the patient to a depth of more than 2 mm, more preferably more than 5 mm, even more preferably more than 10 mm.

It is preferred that the access device further comprises a fluid reservoir which is in fluid contact with the needle. A preferred fluid reservoir is a syringe with a plunger. Alternatively a flexible bag is used as a fluid reservoir. Preferably, the walls of the flexible bag are not elastic and do not create a pressure on the fluid. Alternatively a cartridge is used as a fluid reservoir. Alternatively an infusion line is connected or connectable to the access device. In a preferred embodiment, the reservoir or the infusion line are connected to the access device via the connection fitting.

In a preferred embodiment of the invention, the access device further comprises a spring element. In the context of the present invention a spring element is any element that can provide a restoring force, pushing the needle towards the first position. A preferred spring element is a helical spring which preferably is arranged coaxially with the needle. It is preferred that one end of the helical spring is in contact with the base. Preferably the other end is in contact with the hub of the needle. Preferably, the motion of the needle from the first to the second position contracts the spring and thus the restoring force is generated which acts on the needle pushing it back towards the first position once the manual force applied by the user is released. The achievable advantage of a helical spring arranged coaxially with the needle is that the force almost exclusively acts along the axis of the needle. This way it can be avoided that the linear motion of the needle in the base is disturbed. Moreover, helical springs are very cheap and can be manufactured in almost any size with a wide range of spring constants. A preferred spring generates a restoring force equivalent to a few grams, preferably more than ten grams, even more preferably more than 50 grams, when fully contracted. In an alternative embodiment, the spring element is a leaf spring. In an alternative embodiment, the spring element comprises or consists of an elastomeric substance, for example a rubber block or the like. In another alternative embodiment, the spring element is missing and the restoring force is performed manually by the user. In a preferred embodiment of the access device the second position is adjustable. Preferably, the second position is adjustable in the direction of motion of the needle from the first to the second position. An achievable advantage of an adjustable second position is that the stroke of the needle and/or the depth of penetration of the cannula can be adjusted. It is preferred that the second position is continuously adjustable. Further it is preferred that the adjustment range of the second position is at least 1 mm, preferably 10 mm, even more preferably 20 mm. Advantageously, the user can adjust the injection depth in order to choose between for example an intradermal or subcutaneous injection. Alternatively, the second position is adjustable in several discrete steps. A preferred embodiment comprises two or more, preferably three or more even more preferably five or more adjustment steps. A preferred embodiment comprises one adjustment for an intradermal injection, one adjustment for a subcutaneous and one adjustment for an intramuscular injection.

In a preferred embodiment of the invention the locking mechanism is adapted to lock the needle in at least one more discrete position. The preferred access device therefore comprises at least four, preferably five, more preferably six even more preferably seven or more positions. Preferably each position is located between the first and second position of the needle. It is preferred that the locking mechanism does not engage in either of the intermediate positions when the needle is moved from the first towards the second position. Preferably when retracting the needle from the second towards the first position, the locking mechanism engages at each of the discrete positions 3, 4, 5, 6 and 7. Preferably the actuator allows manually disengaging the locking mechanism at each of the discrete locking positions.

BRIEF DESCRIPTION OF THE DRAWINGS

The invention is illustrated in greater detail with the aid of a schematic drawing.

FIG. 1 shows a perspective view of an embodiment of the invention.

FIGS. 2*a-f* illustrate the mechanism of an embodiment of the invention.

FIGS. 3*a-c* show a side view of an embodiment of the invention in the three different positions.

FIGS. 4*a-f* illustrate the mechanism of the cam and the cam follower.

FIG. 5*a-c* show an embodiment of the invention with an adjustable second position in perspective and sectional views.

FIG. 6 shows an embodiment of the invention with a fourth and a fifth discrete position of the needle.

DETAILED DESCRIPTION OF THE EMBODIMENTS OF THE INVENTION

Figure 1:
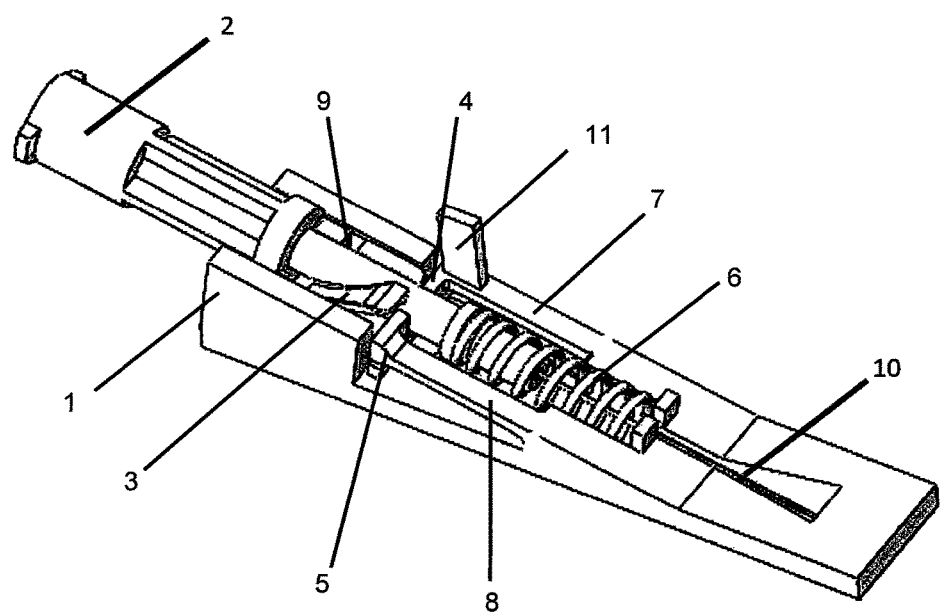
FIG. 1.

In FIG. 1 an embodiment of an access device is depicted, comprising a base 1 which has an essentially flat bottom surface for alignment of the access device with the skin of a patient. In the base 1 a needle for puncturing the skin is arranged. The needle comprises a hub 2 and a cannula 10. The tip of the cannula 10 has a bevel facing upwards. The needle is movably mounted in the base 1 such that it can slide linearly in axial direction between a first, fully retracted, and a second, maximally extended, position. The needle of the displayed access device is in the first, fully retracted, position such that the cannula 10 does not protrude from the base 1. Further, a locking mechanism is provided which engages when the needle retracts from the second position and reaches a discrete third position, inhibiting the needle from further retracting to the first position and from moving backwards to the second position. The access device of the illustrated embodiment is actuatable by means of a mechanical actuator 11 which is provided for disengaging the locking mechanism. The actuator 11 is arranged together with a lock pin 4 on a lock pin spring 7. The hub 2 comprises a Luer-lock fitting for connection of a syringe or infusion line with a corresponding Luer-lock fitting. The syringe is not shown in the illustrations for reason of visualization. A helical spring 6 is arranged coaxially with the needle providing a restoring force and pushing the needle towards the first position. The locking mechanism comprises a cam 3 which is arranged on the hub 2, and a cam follower 5 arranged on the base 1. A lock notch 9, with which the lock pin 4 can engage, is arranged in the hub 2. The cam 3 and the cam follower 5 are adapted to convert the linear motion of the needle with respect to the base 1 into an auxiliary action. This auxiliary action only occurs for one direction of motion of the needle with respect to the base 1. The auxiliary action is to prevent the engagement of the lock mechanism when the needle is moving from the first to the second position.

Figure 2:
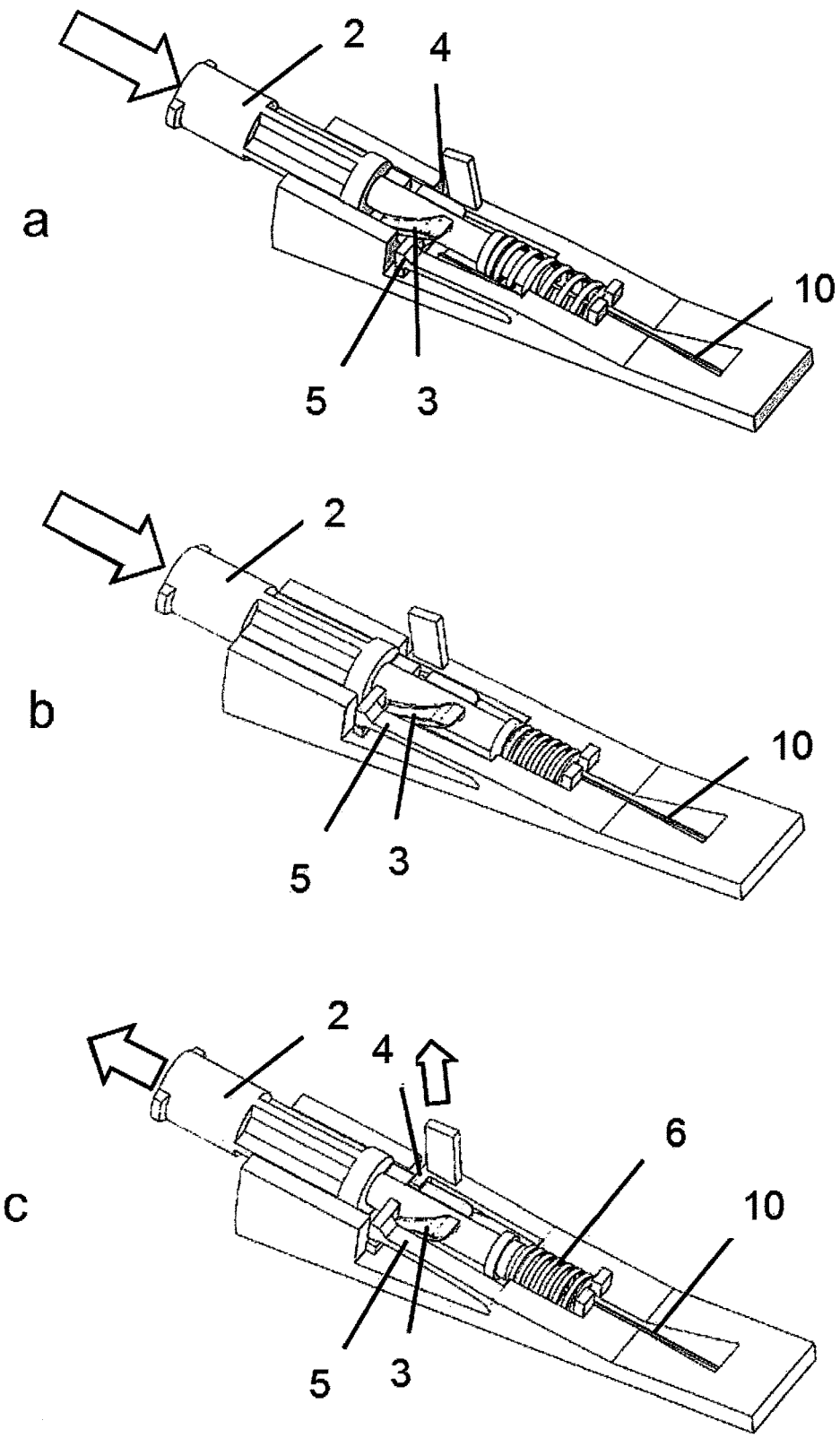
FIG. 2.
Figure 2:
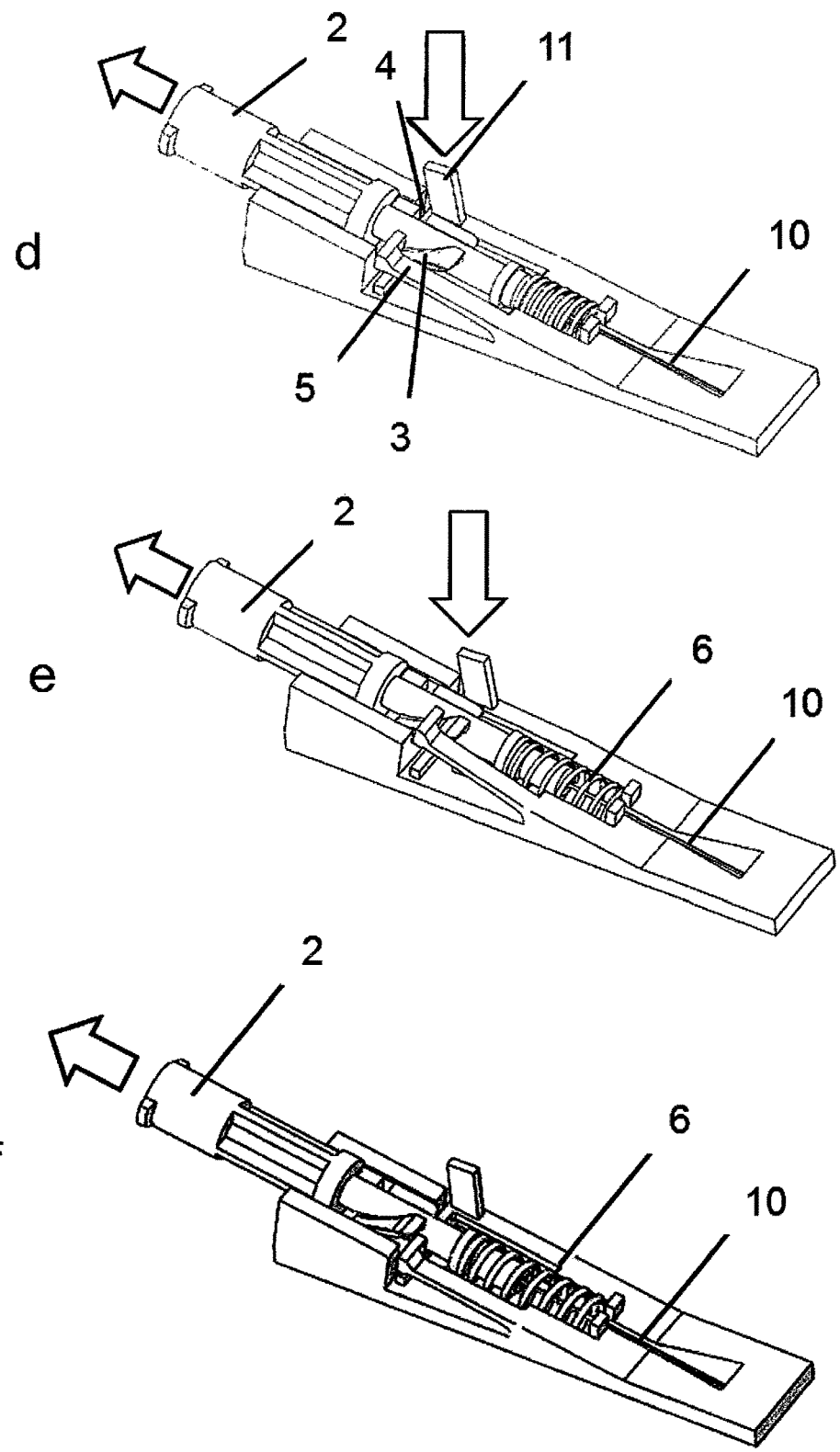

The mechanism of the access device depicted in FIG. 1 is further illustrated in FIGS. 2*a* to *f*. FIG. 2*a* shows the access device when a manual force is applied to the hub 2 along the axis of the needle. The needle moves against the force of the spring 6 towards the second position. The cam 3 which is arranged on the hub 2 moves along the top of the cam follower 5 pressing down the cam follower 5. The cam follower 5 is pressed down against a bridge which is connected to the lock pin 4, preventing the lock pin 4 from engaging with the lock notch 9. In FIG. 2*b* the needle is in the second, maximally extended position. At this point the cam follower 5 is allowed to rise above the cam 3. In FIG. 2*c* the manual force applied to the hub 2 is released and the needle retracts due to the force applied by the spring 6. As the cam follower 5 no longer presses down the lock pin 4 via the bridge, the lock pin 4 engages with the lock notch 9 once the third position is reached. This third position is one injection position. The locking mechanism inhibits the needle from moving in either direction. The cannula 10 is now at its designed penetration depth for the intended dermal injection. The arrow in FIG. 2*d* indicates that the user now pushes down the actuator 11 and thus disengages the locking mechanism. Hereby the user can conveniently start the full retraction of the needle after the injection has been applied. FIG. 2*e* shows a position midway between the third and the first position. The needle is being forced back by the spring 6. Finally FIG. 2*f* shows the access device with the needle returned to the first position, fully retracted in the base. The access device can now be removed from the skin of the patient without hazard of injury.

Figure 3:
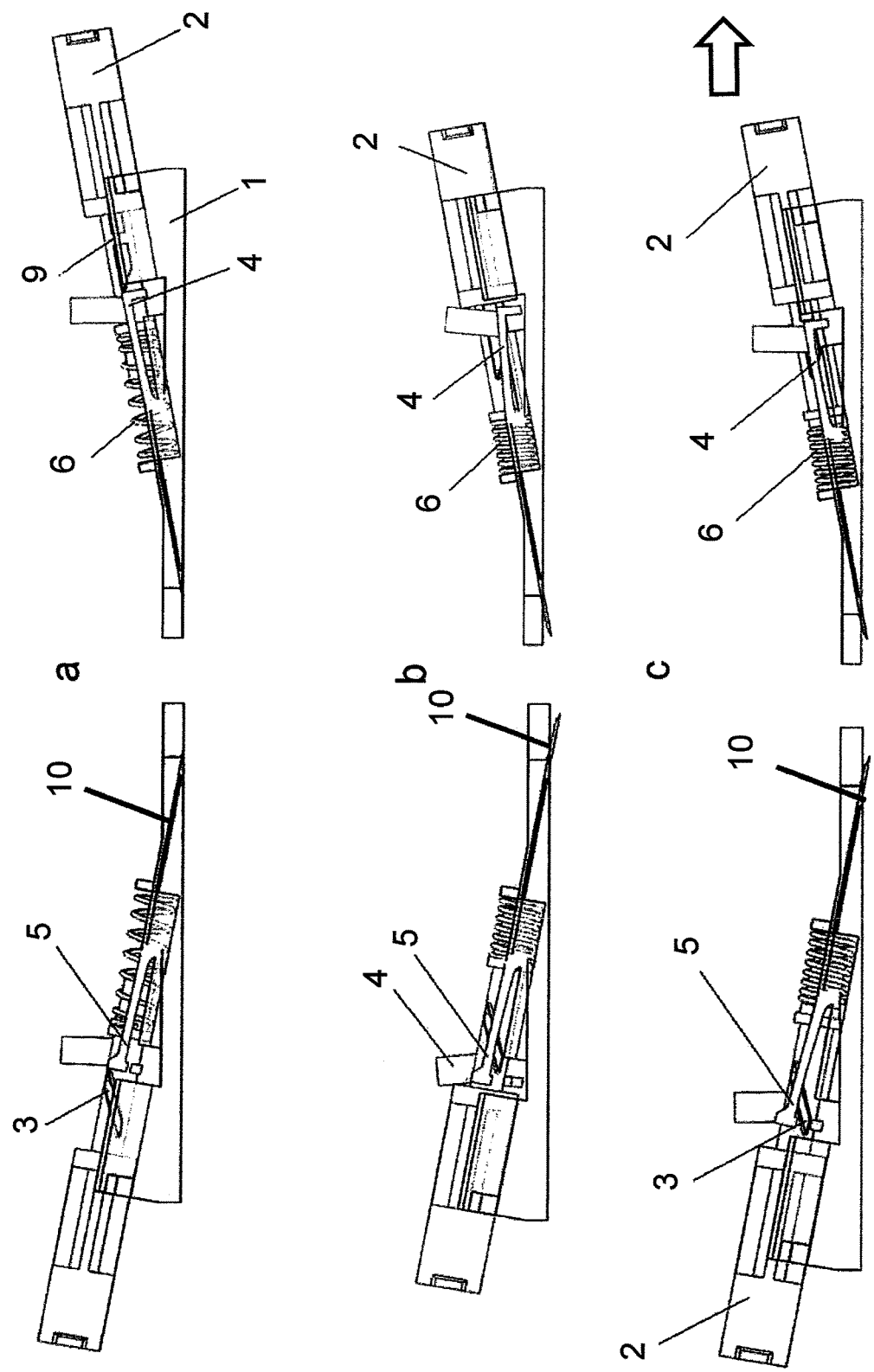
FIG. 3.

FIGS. 3*a* to *c* show side views of the three characteristic positions of the needle of the embodiment of the access device. On the bottom surface, the base 1 comprises a pressure sensitive adhesive for fixating the base 1 on the skin of a patient (not shown). FIG. 3*a* shows the first, fully retracted position of the needle. This is the initial position when the needle is inside the base 1 such that an accidental contact with the tip of the cannula 10 is prevented. FIG. 3*b* shows the second, maximally extended, position of the needle. In this position the cannula 10 protrudes about 5 mm from the bottom surface of the base 1. FIG. 3*c* shows the third position when the needle is slightly retracted and ready for infection. The tip of the cannula 10 is now approximately 1 mm under the surface of the skin, which is a typical depth for application of an intradermal injection. Also clearly visible in the side view is the needle bevel and its orientation. The bevel angle is approximately 30°. In the displayed embodiment the needle is arranged with a puncturing angle of approximately 10°. This is a typical angle that also a physician would choose to apply an intradermal injection.

Figure 4:
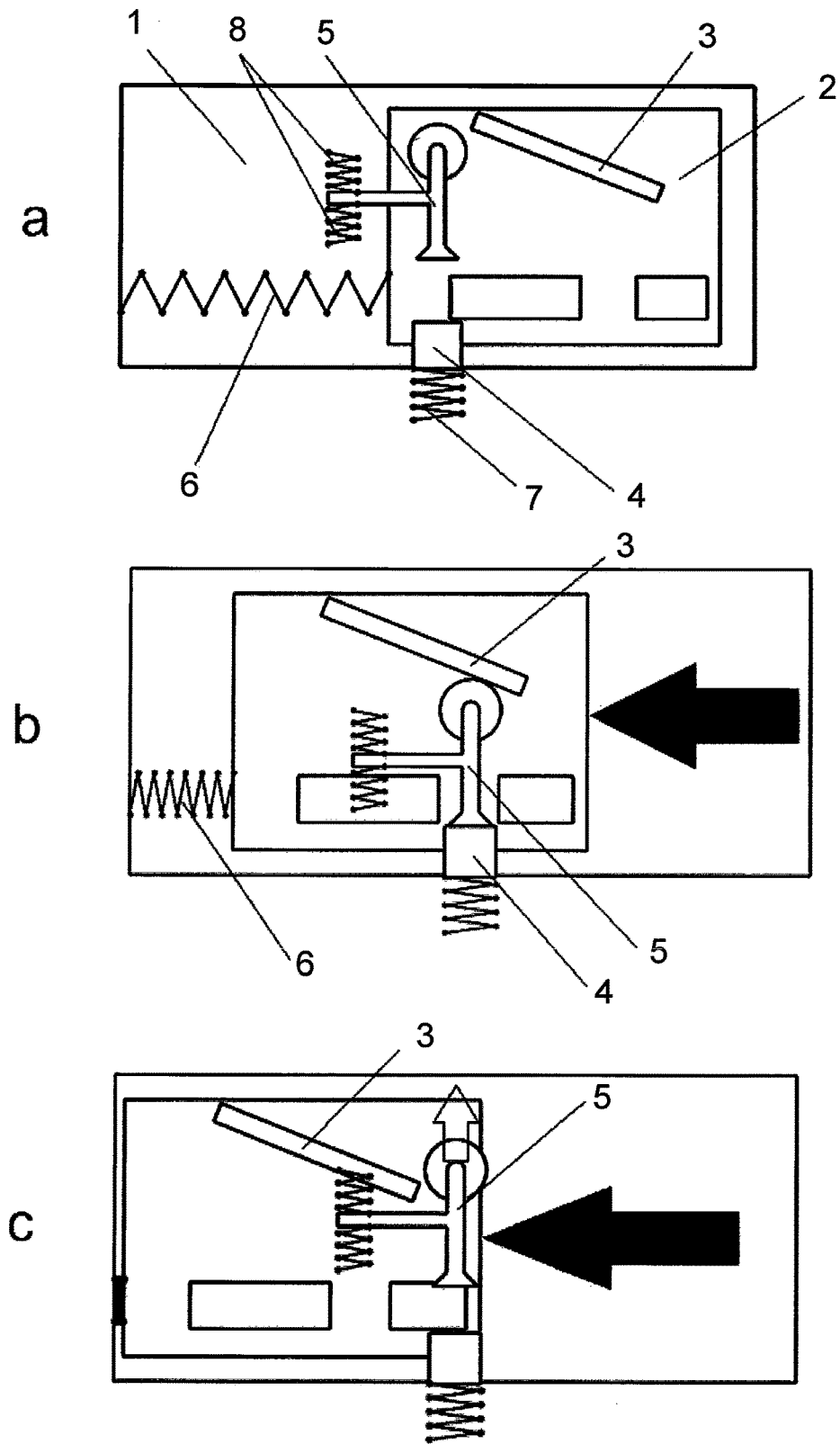
FIG. 4.
Figure 4:
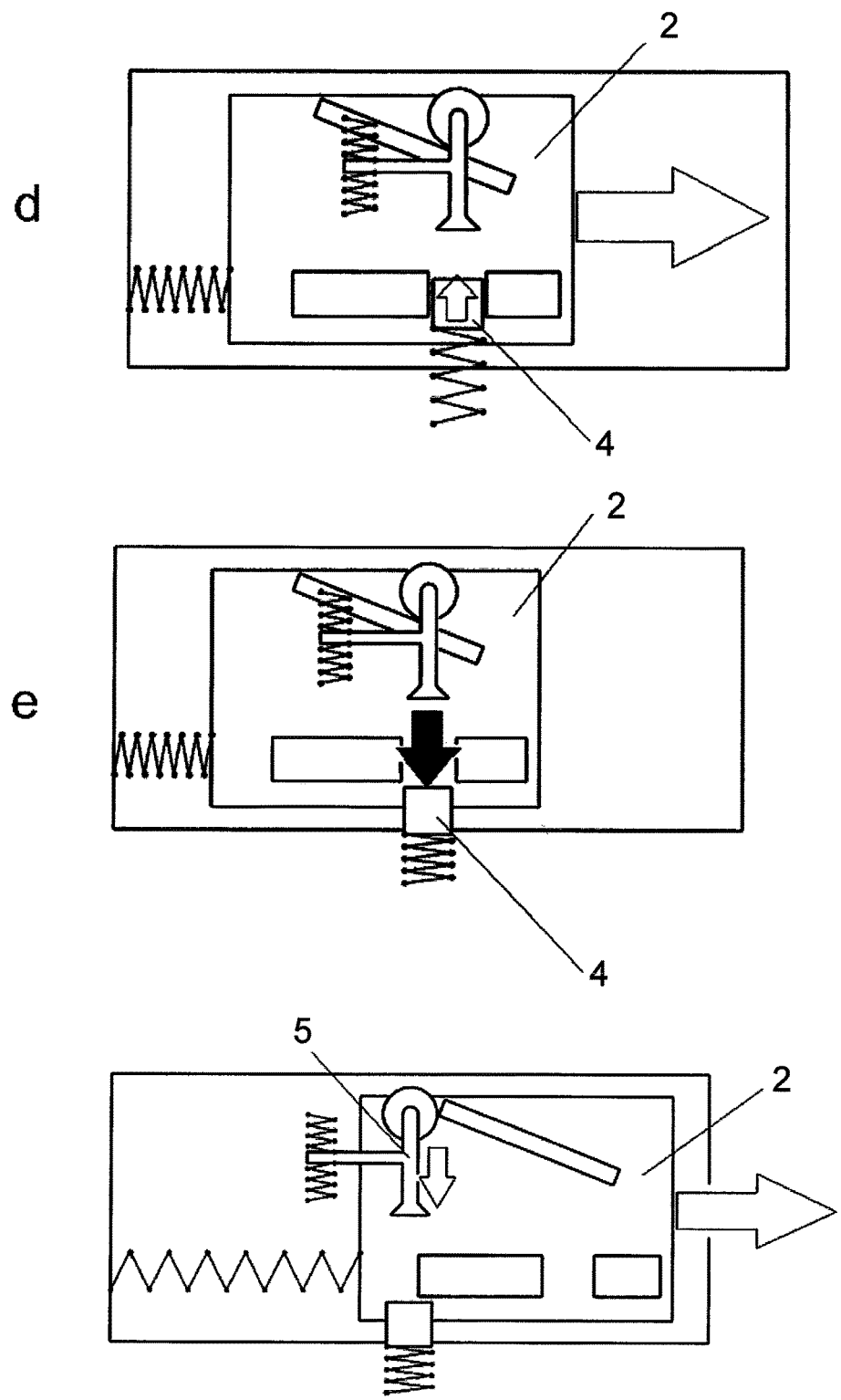

In FIGS. 4*a* to f the locking mechanism is further illustrated by schematic drawings. FIG. 4*a* starts with the first, fully retracted, position. The cam follower 5 is in a neutral position and the spring 6 is in its extended state. In FIG. 4*b* the hub 2 is manually pushed forward relative to the base 1 and against the spring force whereby the cam follower 5 follows the contour of the cam 3, preventing the lock pin 4 from engaging with the lock notch 9. FIG. 4*c* shows the position in which the needle would be in the second, maximally extended, position. The spring 6 is maximally compressed. At this position the cam follower 5 is allowed to move back to its neutral position. In FIG. 4*c* the manual pressure on the hub 2 is released and the hub 2 is forced back by the spring force. The cam follower 5 is now on the other side of the cam 3 and thus is pushed away from the lock pin 4 which is therefore allowed to engage with the lock notch 9. The hub 2 is now in the third position at which the injection is to be applied. The lock pin 4, engaged with the lock notch 9, inhibits the hub 2 from moving in either direction. The arrow in FIG. 4e illustrates the actuator 11 which disengages the locking mechanism so that the hub 2 can move back to the first, fully retracted, position shown in FIG. 4f. The cam follower 5 is also released again and moves back to its neutral position and the spring 6 is maximally extended.

Figure 5:
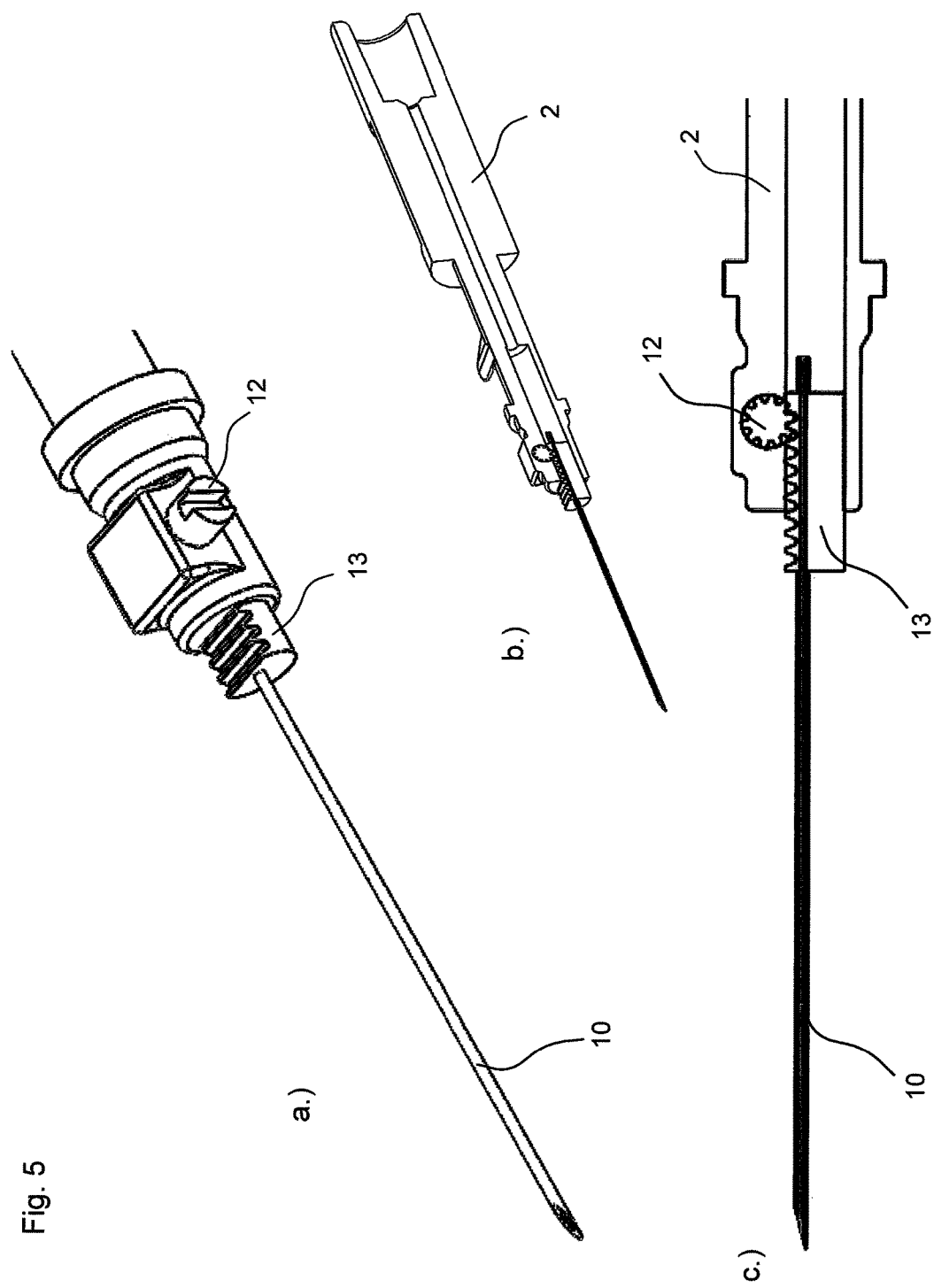
FIG. 5.

Another embodiment of the invention is depicted in FIG. 5a to c. FIG. 5 a shows a perspective view and FIG. 5b and c show corresponding sectional views of the embodiment. This embodiment comprises a mechanism which facilitates adjustment of the second position. The access device comprises a needle with a hub 2 which allows adjusting the length with which the cannula 10 protrudes form the hub 2, thus controlling also the total length of the needle. The mechanism for adjusting the protruding length of the cannula 10 is implemented by means of a rack and pinion as depicted in FIG. 5c. The cannula 10 comprises a sleeve 13 which is arranged such that it can slide in and out of the hub 2. The sleeve 13 further comprises a plurality of teeth that function as a rack that is adapted to interact with a corresponding pinion. The pinion is implemented as an adjustment screw 12 which is accessible from the outside as shown in FIG. 5a. By turning the adjustment screw 12, for example by using a screwdriver, the cannula 10 can be linearly adjusted within a range of about 10 mm along the axis of the needle. The more the cannula 10 protrudes from the hub 2, the deeper it can penetrate into the patient. In this embodiment the second position is adjustable continuously. With this embodiment of the invention, intradermal or subcutaneous injection can be applied, depending on the setting of the adjustment screw 12.

Figure 6:
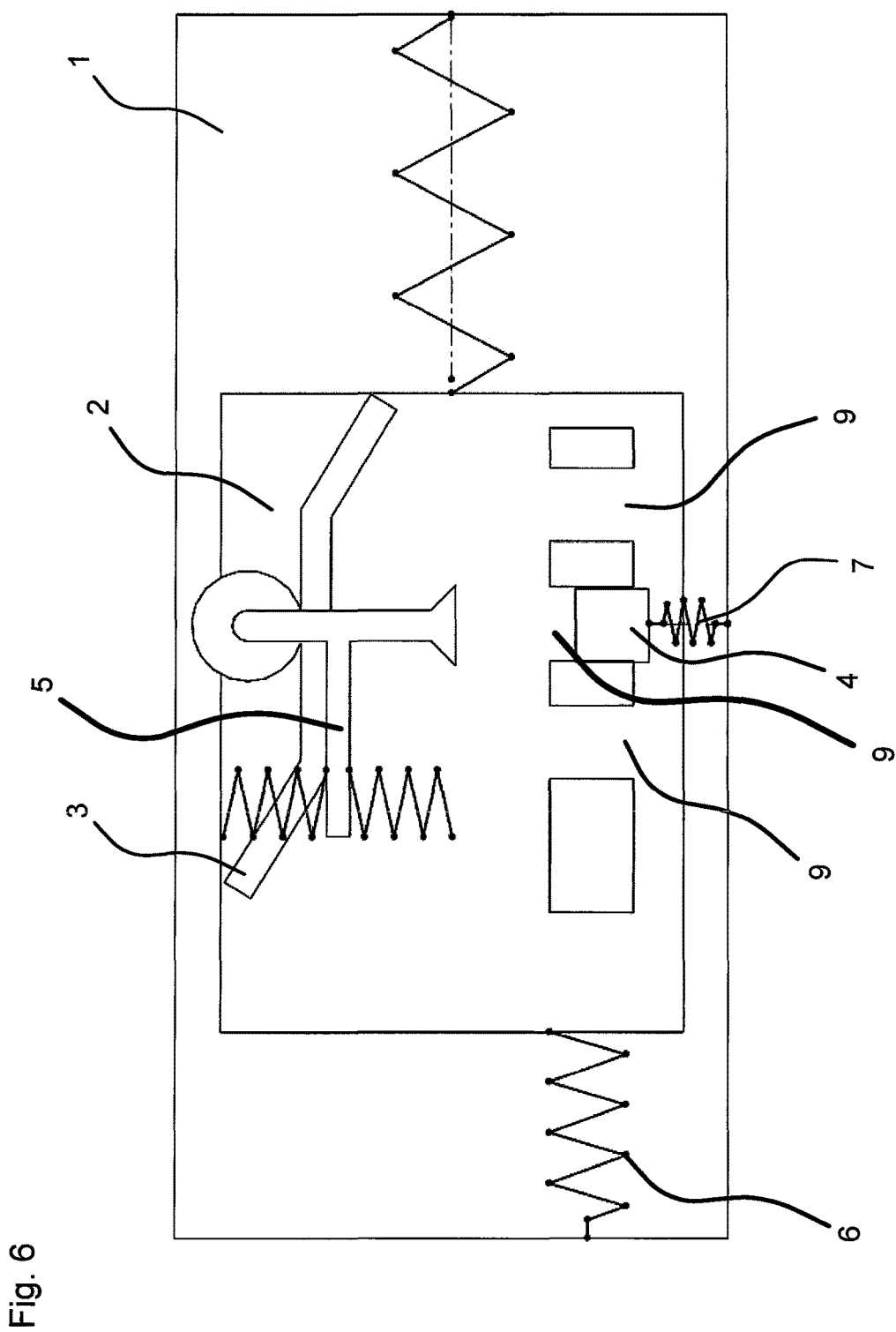
FIG. 6.

A further embodiment of the invention is illustrated schematically in FIG. 6. Here the locking mechanism is adapted to lock the needle in three different discrete lock positions, namely position three, position four and position five, located between the first and the second position. Similar to the mechanism shown in FIG. 4, the cam follower 5 is adapted to prevent the lock pin 4 from engaging when the hub is moved from the first towards the second position. In this embodiment the cam 3 is adapted to keep the cam follower 5 in a position where it prevents the lock pin 4 from engaging with the three consecutive lock notches 9. When the cam follower 5 is on the other side of the cam 3 (as seen in FIG. 6), it does not prevent the lock pin 4 from engaging with the three different lock notches 9 anymore. While the needle is retracted from the second towards the first position the lock pin 4 engages each time a lock position is reached, locking the needle at that discrete position. By means of the actuator 11 (not shown in FIG. 6), the locking mechanism can be disengaged again, allowing the needle to be moved further towards the first position.

The features described in the above description, claims and figures can be relevant to the invention in any combination. Their reference numerals in the claims have merely been introduced to facilitate reading of the claims. They are by no means meant to be limiting.

LIST OF REFERENCE NUMERALS

1 Base
2 Hub
3 Cam
4 Lock pin
5 Cam follower
6 Spring
7 Lock pin spring
8 Cam follower spring
9 Lock notch
10 Cannula
11 Actuator
12 Adjustment screw
13 Sleeve

The invention claimed is:
1. An access device comprising:
   a base for aligning the access device with the skin of a patient;
   a needle for puncturing the skin, the needle comprising a hub and a cannula, and the needle being movably mounted in the base such that the needle can move between a first, fully retracted position, and a second, maximally extended, position; and
   a locking mechanism comprising a cam, a cam follower and a locking member, wherein the locking mechanism is adapted to lock the needle in a discrete third position located between the first position and the second position, the third position being an injection position, such that the locking mechanism, when engaged, inhibits motion of the needle in both moving directions;
       wherein the cam and the cam follower are adapted to convert the motion of the needle with respect to the base into a motion of the cam follower, wherein the cam follower prevents the engagement of the locking member when the needle is moving from the first to the second position, preventing engagement of the locking mechanism.
2. The access device of claim 1,
   wherein the cam is arranged on the hub and the cam follower is arranged on the base.
3. The access device of claim 1, wherein the hub of the needle has a connection fitting.
4. The access device of claim 1, wherein the needle creates a puncture angle with respect to the skin surface when puncturing the skin, the puncture angle not exceeding 60° or being between 70° and 110°.
5. The access device of claim 1, wherein the base comprises adhesive means for fixating the base on the skin of the patient.
6. The access device of claim 1, wherein the cannula of the needle is adapted to protrude no more than 100 mm from the bottom surface of the access device in axial direction or more than 10 mm measured perpendicularly to the surface of the skin.
7. The access device of claim 1, wherein the access device further comprises a fluid reservoir which is in fluid contact with the needle.
8. The access device of claim 1, wherein the access device further comprises a spring element providing a restoring force pushing the needle towards the first position.
9. The access device of claim 1, wherein the second position is adjustable.
10. The access device of claim 1, wherein the locking mechanism is adapted to lock the needle in at least one more discrete position.
11. The access device of claim 1, wherein the access device is actuatable to disengage the locking mechanism, whereby the needle retracts towards the first position.

12. An access device comprising:
a base for aligning the access device with the skin of a patient;
a needle for puncturing the skin, the needle comprising a hub and a cannula, and the needle being movably mounted in the base such that the needle can move between a first, fully retracted position, and a second, maximally extended, position; and
a locking mechanism comprising a cam, a cam follower and a locking member, wherein the locking mechanism is adapted to lock the needle in a discrete third position located between the first position and the second position, the third position being an injection position, such that the locking mechanism, when engaged, inhibits motion of the needle in both moving directions;
wherein the locking mechanism comprises a cam, a cam follower, a transfer mechanism and a locking member, wherein the cam and the cam follower are adapted to convert the motion of the needle with respect to the base into a motion of the cam follower, wherein the cam follower acts on the transfer mechanism and the transfer mechanism prevents the engagement of the locking member when the needle is moving from the first to the second position, preventing the engagement of the locking mechanism.

* * * * *